United States Patent
Slivka et al.

(10) Patent No.: US 7,524,335 B2
(45) Date of Patent: *Apr. 28, 2009

(54) FIBER-REINFORCED, POROUS, BIODEGRADABLE IMPLANT DEVICE

(75) Inventors: Michael A. Slivka, Taunton, MA (US); Gabriele G. Niederauer, San Antonio, TX (US); Kristine Kieswetter, San Antonio, TX (US); Neil C. Leatherbury, San Antonio, TX (US)

(73) Assignee: Smith & Nephew, Inc., Memphis, TN (US)

( * ) Notice: Subject to any disclaimer, the term of this patent is extended or adjusted under 35 U.S.C. 154(b) by 131 days.

This patent is subject to a terminal disclaimer.

(21) Appl. No.: 10/931,474

(22) Filed: Aug. 31, 2004

(65) Prior Publication Data

US 2005/0240281 A1    Oct. 27, 2005

Related U.S. Application Data

(60) Continuation-in-part of application No. 10/288,400, filed on Nov. 4, 2002, now Pat. No. 6,783,712, which is a division of application No. 09/426,686, filed as application No. PCT/US98/11007 on May 29, 2008, now Pat. No. 6,511,511.

(60) Provisional application No. 60/048,320, filed on May 30, 1997.

(51) Int. Cl.
*A61F 2/02* (2006.01)

(52) U.S. Cl. .............. 623/23.75; 623/11.11; 623/16.11

(58) Field of Classification Search ............. 623/23.75, 623/11.11, 16.11, 23.34, 23.51, 23.63, 23.76; 424/426; 523/113

See application file for complete search history.

(56) References Cited

U.S. PATENT DOCUMENTS

| | | | | | |
|---|---|---|---|---|---|
| 1,009,448 | A | * | 11/1911 | Simon | 73/861.54 |
| 1,120,122 | A | * | 12/1914 | Betts | 223/81 |
| 1,331,018 | A | * | 2/1920 | Luthy | 429/143 |

(Continued)

FOREIGN PATENT DOCUMENTS

EP         0277678         8/1988

(Continued)

OTHER PUBLICATIONS

Bucholz, R.W. et al. (Mar. 1994) "Fixation with bioabsorbable screws for the treatment of fractures of the ankle," J. Bone Joint Surg. 76-A(3):319-324.

(Continued)

*Primary Examiner*—Paul Prebilic
(74) *Attorney, Agent, or Firm*—Norman F. Hainer, Jr.

(57) ABSTRACT

A fiber-reinforced, polymeric implant material useful for tissue engineering, and method of making same are provided. The fibers are preferably aligned predominantly parallel to each other, but may also be aligned in a single plane. The implant material comprises a polymeric matrix, preferably a biodegradable matrix, having fibers substantially uniformly distributed therein. Inorganic particles may also be included in the implant material. In preferred embodiments, porous tissue scaffolds are provided which facilitate regeneration of load-bearing tissues such as articular cartilage and bone. Non-porous fiber-reinforced implant materials are also provided herein useful as permanent implants for load-bearing sites.

18 Claims, 10 Drawing Sheets

U.S. PATENT DOCUMENTS

| | | | | |
|---|---|---|---|---|
| 3,475,077 | A | * | 10/1969 | Buchman .................... 359/247 |
| 3,627,859 | A | * | 12/1971 | Mesite et al. ................. 264/49 |
| 3,662,405 | A | * | 5/1972 | Bortz et al. ............... 623/23.51 |
| 4,103,002 | A | * | 7/1978 | Hench et al. ................ 428/155 |
| 4,234,972 | A | * | 11/1980 | Hench et al. ............. 623/23.57 |
| 4,237,559 | A | * | 12/1980 | Borom ..................... 623/23.51 |
| 4,279,249 | A | * | 7/1981 | Vert et al. ..................... 606/77 |
| 4,338,072 | A | * | 7/1982 | Milford et al. .............. 425/371 |
| 4,411,027 | A | * | 10/1983 | Alexander et al. ........ 623/13.18 |
| 4,478,904 | A | * | 10/1984 | Ducheyne et al. ......... 428/294.4 |
| 4,553,272 | A | * | 11/1985 | Mears ........................ 623/1.4 |
| 4,562,112 | A | * | 12/1985 | Lee et al. .................. 428/318.6 |
| 4,655,777 | A | * | 4/1987 | Dunn et al. .................. 424/423 |
| 4,676,796 | A | * | 6/1987 | Merwin et al. ................. 623/10 |
| 4,743,257 | A | * | 5/1988 | Tormala et al. .......... 623/23.58 |
| 4,775,646 | A | * | 10/1988 | Hench et al. .................... 501/2 |
| 4,851,046 | A | * | 7/1989 | Low et al. ..................... 106/35 |
| 4,863,472 | A | * | 9/1989 | Tormala et al. .......... 623/23.58 |
| 4,965,128 | A | * | 10/1990 | Greidanus et al. ........... 428/398 |
| 4,968,317 | A | * | 11/1990 | Tormala et al. ................ 606/77 |
| 5,074,916 | A | * | 12/1991 | Hench et al. .................. 106/35 |
| 5,206,023 | A | * | 4/1993 | Hunziker ..................... 424/423 |
| 5,218,087 | A | * | 6/1993 | Suzuki et al. ............... 528/503 |
| 5,258,043 | A | * | 11/1993 | Stone ........................... 264/108 |
| 5,290,494 | A | * | 3/1994 | Coombes et al. .............. 264/41 |
| 5,306,311 | A | * | 4/1994 | Stone et al. ............... 623/14.12 |
| 5,338,772 | A | * | 8/1994 | Bauer et al. .................. 523/115 |
| 5,397,572 | A | * | 3/1995 | Coombes et al. ............. 424/426 |
| 5,431,652 | A | * | 7/1995 | Shimamoto et al. ........... 606/76 |
| 5,464,363 | A | * | 11/1995 | Schulz ........................ 451/190 |
| 5,486,598 | A | * | 1/1996 | West et al. ................... 530/338 |
| 5,492,697 | A | * | 2/1996 | Boyan et al. ............. 623/16.11 |
| 5,552,454 | A | * | 9/1996 | Kretschmann et al. ...... 523/113 |
| 5,607,474 | A | * | 3/1997 | Athanasiou et al. ...... 623/23.71 |
| 5,609,638 | A | * | 3/1997 | Price et al. ................ 623/20.32 |
| 5,626,861 | A | * | 5/1997 | Laurencin et al. ........... 424/426 |
| 5,656,450 | A | * | 8/1997 | Boyan et al. ............. 435/68.1 |
| 5,679,723 | A | * | 10/1997 | Cooper et al. ................ 523/115 |
| 5,697,980 | A | * | 12/1997 | Otani et al. .................. 424/423 |
| 5,716,413 | A | * | 2/1998 | Walter et al. ................. 424/423 |
| 5,741,329 | A | * | 4/1998 | Agrawal et al. .............. 424/423 |
| 5,817,328 | A | * | 10/1998 | Gresser et al. ............... 424/426 |
| 5,821,285 | A | * | 10/1998 | Khor et al. ..................... 524/27 |
| 5,830,493 | A | * | 11/1998 | Yokota et al. ................ 424/426 |
| 5,863,297 | A | * | 1/1999 | Walter et al. ............. 623/17.18 |
| 5,876,452 | A | * | 3/1999 | Athanasiou et al. ...... 623/23.72 |
| 5,899,939 | A | * | 5/1999 | Boyce et al. ............. 623/16.11 |
| 5,904,717 | A | * | 5/1999 | Brekke et al. ............... 424/423 |
| 5,919,808 | A | * | 7/1999 | Petrie et al. .................. 514/372 |
| 5,922,753 | A | * | 7/1999 | Petrie et al. .................. 514/447 |
| 5,939,444 | A | * | 8/1999 | Petrie et al. .................. 514/367 |
| 5,947,893 | A | * | 9/1999 | Agrawal et al. ............... 600/36 |
| 5,977,204 | A | * | 11/1999 | Boyan et al. ................. 523/113 |
| 6,071,530 | A | * | 6/2000 | Polson et al. ................ 424/426 |
| 6,187,047 | B1 | * | 2/2001 | Kwan et al. ............... 623/16.11 |
| 6,187,329 | B1 | * | 2/2001 | Agrawal et al. .............. 424/426 |
| 6,241,771 | B1 | * | 6/2001 | Gresser et al. ............ 623/17.16 |
| 6,281,257 | B1 | * | 8/2001 | Ma et al. ...................... 521/61 |
| 6,296,667 | B1 | * | 10/2001 | Johnson et al. .......... 623/23.61 |
| 6,344,496 | B1 | * | 2/2002 | Niederauer et al. ......... 523/113 |
| 6,348,069 | B1 | * | 2/2002 | Vacanti et al. ............ 623/11.11 |
| 6,395,293 | B2 | * | 5/2002 | Polson et al. ................ 424/426 |
| 6,451,059 | B1 | * | 9/2002 | Janas et al. ............... 623/23.51 |
| 6,454,811 | B1 | * | 9/2002 | Sherwood et al. ........ 623/23.76 |
| 6,479,565 | B1 | * | 11/2002 | Stanley ........................ 523/114 |
| 6,511,511 | B1 | * | 1/2003 | Slivka et al. .............. 623/23.75 |
| 6,527,810 | B2 | * | 3/2003 | Johnson et al. .......... 623/23.56 |
| 6,783,712 | B2 | * | 8/2004 | Slivka et al. ................... 264/51 |
| 2001/0008980 | A1 | * | 7/2001 | Gresser et al. ............ 623/17.11 |
| 2001/0039453 | A1 | * | 11/2001 | Gresser et al. ............ 623/17.11 |
| 2001/0053937 | A1 | * | 12/2001 | Johnson et al. .......... 623/23.34 |
| 2002/0035401 | A1 | * | 3/2002 | Boyce et al. ............. 623/23.51 |
| 2002/0131989 | A1 | * | 9/2002 | Brown et al. ................. 424/428 |
| 2002/0143403 | A1 | * | 10/2002 | Vaidyanathan et al. ... 623/23.51 |
| 2003/0023306 | A1 | * | 1/2003 | Liu et al. .................. 623/17.11 |
| 2003/0036800 | A1 | * | 2/2003 | Meredith ................. 623/23.63 |
| 2003/0049329 | A1 | * | 3/2003 | Lee et al. ..................... 424/602 |
| 2005/0177245 | A1 | * | 8/2005 | Leatherbury et al. ....... 623/23.5 |

FOREIGN PATENT DOCUMENTS

| | | |
|---|---|---|
| EP | 0277678 A1 * | 8/1988 |
| EP | 475077 | 3/1992 |
| EP | 0784985 | 4/1996 |
| EP | 1009448 | 3/1999 |
| EP | 1120122 | 4/2000 |
| JP | 61-213047 | 9/1986 |
| JP | 4-64363 | 2/1992 |
| JP | 10286861 | 10/1998 |
| WO | 9117777 | 11/1991 |
| WO | 9713533 | 4/1997 |
| WO | 9824483 | 6/1998 |
| WO | 9835631 | 8/1998 |
| WO | 9846164 | 10/1998 |
| WO | 9847485 | 10/1998 |
| WO | 9853768 | 10/1998 |
| WO | 0035511 | 6/2000 |
| WO | 0076486 | 12/2000 |
| WO | WO-2001/32072 A2 * | 5/2001 |
| WO | 0168005 | 9/2001 |
| WO | 0132072 | 10/2001 |
| WO | 0202156 | 1/2002 |
| WO | 0205750 | 1/2002 |
| WO | 03024316 | 3/2003 |
| WO | 03026714 | 3/2003 |
| WO | 03030956 | 4/2003 |

OTHER PUBLICATIONS

Buckwalter, J.A. and Mankin, H.J. (1998), "Articular cartilage: Degeneration and osteoarthritis, repair, regeneration and transplantation," In American Academy of Orthopaedic Surgery Instructional Course Lectures, W.D. Cannon, Jr., ed., Rosemont, Am. Academy of Orth. Surgeons, 47:487-504.

Cornell, C.N. et al. (1991) "Multicenter trial of Collagraft as bone graft substitute," J. Orthop. Trauma 5(1):1-8.

deGroot, K. (1981), Biocompatibility of clinical implant materials, D.F. Williams, editor, pp. 199-222.

deGroot, K. et al. (1988), "Significance of the porosity and physical chemistry of calcium phosphate ceramics," Ann. N.Y. Acad. Sci 523:272-277.

Eling, B. et al. (Oct. 1982), "Biodegradable materials of poly(L-lactic acid): 1. Melt-spun and solution spun fibers," polymer 23:1587-1593.

Engelberg, I. and Kohn, J. (Apr. 1991), "Physio-mechanical properties of degradable polymers used in medical applications: A comparative study," Biomaterials 12:292-304.

Hench, L.L. (1995), "Bioactive Implants," Chemistry and Industry 14:547-550.

Jarcho, M. (Jan. 1986), "Biomaterial aspects of calcium phosphates: properties and applications. Reconstructive implant surgery and implant prosthodontics," Dent. Clin. North Am. 30(1):25-47.

Kumta, S.M. et al. (Jul. 1992), "Absorbable intramedullary implanats for hand fractures, animal experiments and clinical trials," J. Bone Joint Surg. 74-B(4):563-566.

Lane, J.M. and Bostrom, M.P.G. (May 1997), "Bone grafting and new composite biosynthetic graft materials," In American Academy of Orthopaedic Surgeons Instructional Course Lectures, W.D. Cannon, Jr., editor, 48:525-534.

Newman, A.P. (Mar. 1998), "Current concepts: Articular cartilage repair," Am. J. Sports Med. 26(2):309-324.

Roberts, W.E. (1988), "Bone tissue interface," J. Dent. Ed. 52(12):804-8-9.

Schwartz, Z. et al. (Sep. 1996), "Ability of commercial demineralized freeze-dried bone allograft to induce new bone formation," J. Periodontol. 67(9):918-926.

Suominen et al. (Dec. 1996), "Subchondral bone and cartilage repair with bioactive glasses, hydroxyapatite, and hydroxyapatite-glass composite," J. Biomater. Mater. Res. 32:543-551.

van Susante et al. (Dec. 1998), "Chondrocyte-seeded hydroxyapatite for repair of large articular cartilage defects. A pilot study in the goat," Biomaterials 19:2367-2374.

Younger, E.M. and Chapman, M.W. (Mar. 1989), "Morbidity at bone graft donor sites," J. Orthop. Trauma 3(3):192-195.

U.S. Appl. No. 09/702,996, filed Oct. 30, 2000, first inventor G. Niederauer.

Cima et al. (1991) "Tissue Engineering by Cell Transplantation Using Degradable Polymer Substrates," J. Biochem. Eng. 113:143-151.

Fujisato et al. (Jan. 1996) "Effect of Basic Fibroblast Growth Factor on Cartilage Regeneration in Chondrocyte-seeded Collagen Sponge Scaffold," Biomater. 17:155-162.

Hodge et al. (1986) "Contact Pressures in the Human Hip Joint Measured in vivo," Proc. Natl. Acad. Sci. USA 83:2879-2833.

Kempson, G.E. (1980) "The Mechanical Properties of Articular Cartilage," In; The Joints and Synovial Fluid, vol. II, Academic Press, pp. 177-238.

Mikos et al. (1993) "Preparation of Poly9glycolic acid) Bonded Fiber Structures for Cell Attachemnt and Transplantation," J. Biomed. Mater. Res. 27:183-189.

Schakenraad et al. (1988) "Biodegradable Hollow Fibers for the Controlled Release of Drugs," Biomat. 9:116-120.

Slivka et al. (Dec. 2001) "Porous, Resorbable, Fiber-Reinforced Scaffolds Tailored for Articular Cartilage Repair," Tissue Eng. 7(6):767-781.

Vacanti et al. (1994) "Tissue-Engineered Morphogenesis of Cartilage and Bone by Means of Cell Transplantation Using Synthetic Biodegradable Polymer Matrices," Clinics in Plastic Surgery 24(3):445-462.

Vacanti, C. (1991) "Synthetic Polymers Seeded with Condrocytes Provide a Template for New Cartilage Formation," Plast. Reconstr. Surg. 88:753-759.

* cited by examiner

FIBER-REINFORCED, POROUS, BIODEGRADABLE IMPLANT DEVICE

CROSS-REFERENCE TO RELATED APPLICATIONS

This application is continuation in part of U.S. application Ser. No. 10/288,400, filed Nov. 4, 2002 now U.S. Pat. No. 6,783,712, which is a divisional of U.S. application Ser. No. 09/426,686 filed 25 Oct. 1999 now U.S. Pat. No. 6,511,511, which claims priority to PCT Application PCT/US98/11007 filed 29 May 1998, which claims priority to U.S. Provisional Application No. 60/048,320 filed 30 May 1997, all of which are incorporated herein in their entirety to the extent they are not inconsistent herewith.

BACKGROUND OF THE INVENTION

The potential repair of articular cartilage in human using porous scaffolds has been described. Mears in U.S. Pat. No. 4,553,272 describes a method for osteochondral repair focusing on the use of starter cells, specific pore sizes in a porous scaffold, and providing a barrier between the two pore sizes. There is no mention of the use of biodegradable scaffolds or the necessity of providing a scaffold that can withstand physiological loads. Hunziker in U.S. Pat. No. 5,206,023 teaches a method for articular cartilage repair involving pretreating the defect area with enzymes to remove proteoglycans, then providing a biodegradable carrier (scaffold) to provide proliferation agents, growth factors, and chemotactic agents.

Vert et al. in U.S. Pat. No. 4,279,249 describe a solid biodegradable osteosynthesis device made of a fiber-reinforced composite. The fibrous component is a biodegradable polymer high in glycolide content and the matrix component is high in lactide units. There is no mention of porous devices and the favorable mechanical properties achieved through fiber reinforcement are obtained through typical stacking and layering techniques known in the art. Uniform distribution of fibers throughout the matrix is not disclosed.

The prior art does not appear to teach how to optimize mechanical properties by reinforcing highly porous materials (50%-90% porous). Nijenhuis et al. in European Patent 0 277 678 describe a biodegradable, porous scaffold preferably incorporating biodegradable reinforcing fibers. The scaffold has a bi-porous structure (bimodal pore distribution) made using a combination of solution-precipitation and salt-leaching techniques. Although the fibers are incorporated to "reinforce" the scaffold, no evidence is presented to verify that the mechanical properties are actually improved through such reinforcement and the fibers appear to be randomly aligned.

Stone et al. in U.S. Pat. No. 5,306,311 describe a prosthetic, resorbable articular cartilage composed of a dry, porous, volume matrix of randomly or radially oriented, allegedly biocompatible and bioresorbable fibers. Stone's patent speaks mainly of natural polymeric fibers, such as collagen and elastin, which are harvested and purified from xenogenic sources. The fibers are then cross-linked to provide a cohesive scaffold. The ability of the scaffold to support articulating joint forces is not shown.

All publications and patent applications referred to herein are fully incorporated by reference to the extent not inconsistent herewith.

SUMMARY OF THE INVENTION

This invention provides a fiber-reinforced, polymeric implant material useful for tissue engineering, and method of making same. The implant material preferably comprises a polymeric matrix, preferably a biodegradable matrix, having fibers substantially uniformly distributed therein in predominantly parallel orientation as shown in FIGS. 1 and 2. In an embodiment, the implant further comprises inorganic particles. In preferred embodiments, porous tissue scaffolds are provided which facilitate regeneration of load-bearing tissues such as articular cartilage and bone.

The material of this invention is used to prepare porous, fiber-reinforced, biodegradable tissue scaffolds whose fibrous supports are oriented predominantly in a single direction. The scaffold may be implanted into humans or animals to provide support for physiological loads applied parallel to the predominant direction of orientation of the fibers. For example, in an osteochondral site on the femoral condyle, the primary direction of loading is perpendicular to the surface of the cartilage. The oriented fibers act like struts in a bridge support to provide strength and stiffness to the pore walls of the scaffold and provide a characteristic columnar pore architecture especially suitable for cell ingrowth. The orientation of the fibers also causes the mechanical properties of the scaffold to be anisotropic, i.e., the higher strengths provided by the fibers is maximal in the direction parallel to the fibers, thus providing primary support for physiological loads where they are highest.

Orientation of the fibers is achieved through a dissolution-precipitation process combined with a novel kneading and rolling process. Using various amounts of fiber reinforcement, the mechanical properties of the scaffold may be tailored to the host tissue environment for optimal performance.

Alternatively, the polymer used may be non-biodegradable, and/or the implant may be made non-porous (fully dense) for use as a permanent implant, such as a bone plate in locations requiring load bearing.

The fibers are substantially uniformly distributed throughout the polymer matrix, that is the number of fibers present in a selected portion of the matrix which is large enough to contain several macropores should be substantially the same as (within at least about 20% of) the number of fibers present in any other such selected portion of the matrix. "Macropores" are the larger, columnar-shaped voids formed in the process of manufacturing the material as shown in FIGS. 1 and 2.

The invention may be used for a variety of tissue engineering applications, including osteochondral defect repair, partial and full thickness cartilage defect repair, bone graft substitute, bone graft onlay, ligament or tendon augmentation, oral/maxillofacial surgery, and other reconstructive surgery. The invention is particularly useful for, but not limited to, applications where the implant is to be placed in a defect in a load-bearing tissue, i.e., where stresses applied to the implant once placed in the defect are high in one direction compared to relatively perpendicular directions. One example is in an osteochondral or full thickness cartilage defect, where during such activities as normal walking, there are very high compressive stresses perpendicular to the surface of the cartilage, whereas the stresses parallel to the surface are much less. Another example is alveolar ridge augmentation, where primarily one-directional compressive stresses are due to biting or chewing.

The reinforcing fibers may be made of any suitable biodegradable material by methods known to the art or may be commercially available fibers. Polyglycolide (PGA) fibers are currently available from several sources including Albany International, Sherwood Davis & Geck and Genzyme Surgical Products. Fibers from sutures may also be used, e.g., Vicryl® (90:10 poly [glycolide:lactide]) from Ethicon (Johnson & Johnson). They are preferably synthetic fibers, and are preferably of a length short enough not to interfere with processability, e.g., less than about 1 cm. They can be chopped to the desired length from longer fibers, preferably they have a length between about 0.5 mm and about 1.0 cm and more preferably between about 0.5 mm and about 4.5 mm. The fibers preferably have a diameter between about 5 µm and about 50 µm, more preferably between about 5 µm and about 25 µm.

The reinforcing fibers preferably have mechanical properties that are not substantially compromised when tested in a physiological (aqueous, 37° C.) environment. Any biocompatible material can be used to make the fibers. The fibers are preferably insoluble in the solvent used to dissolve the matrix polymer. For articular cartilage repair, the fibers are preferably made from polyglycolide (PGA) or a glycolide-lactide copolymer with a glycolide content above 80%. For bone repair, the fibers may be made of a biodegradable glass such as calcium phosphate or bioactive ceramic. The volume fraction of fibers within the composite scaffold is preferably between about 5% and about 50%, and more preferably between about 10% and about 30%. The volume fraction of fibers is equal to the volume of fibers divided by the sum of the volume of the polymer matrix, the volume of the fibers and the volume of any inorganic particles present.

The reinforcing fibers used in this invention may alternatively be hollow fibers known to the art. The hollow fibers provide channels to aid in cell and tissue infiltration and can additionally be filled with bioactive agent for delivery to the tissue.

The inorganic particle component of the implant can add both mechanical reinforcement and biological activity to the material. In an embodiment, the particles are substantially uniformly distributed. In an embodiment the inorganic particles are biodegradable. In a different embodiment, the inorganic particles are ceramic particles, mineral particles, or a combination thereof. In an embodiment, the ceramic (or mineral) component is chosen from calcium sulfate (hemi- or di-hydrate form), salts of calcium phosphate such as tricalcium phosphate or hydroxyapatite, various compositions of Bioglass®, and blends or combinations of these materials. Particles can range in size from sub-micron to up to 2 mm, or about 0.5 to about 2000 microns, depending on the desired role of the component chosen. Indifferent embodiments, the size of the particles is between about 8 and about 300 microns or between about 15 and about 50 microns. The volume fraction of inorganic particles can range from about 2% to about 60%, from about 5% to about 50%, or from about 10% to about 40%. The volume fraction of the inorganic particles is the volume of the inorganic particles divided by the sum of the volume of the inorganic particles, the volume of the fibers, and the volume of the polymer matrix.

Incorporation of calcium-containing minerals can help buffer the degradation of biodegradable polymers. Other useful buffering compounds include compounds as disclosed in U.S. Pat. No. 5,741,321 to Agrawal et al., hereby incorporated by reference. Volume fractions of the buffering compound are from about 1% to about 40%, from about 5% to about 30%, or from about 10% to about 20%. Particle sizes for the buffering compound are less than about 2 mm or less than about 1 mm.

Biodegradable polymers or other biodegradable materials known to the art may be used for the biodegradable matrix. Some examples of suitable biodegradable polymers are alpha-polyhydroxy acids, polyglycolide (PGA), poly(L-lactide), poly(D,L-lactide), poly(ε-caprolactone), poly(trimethylene carbonate), poly(ethylene oxide) (PEO), poly(β-hydroxybutyrate) (PHB), poly(β-hydroxyvalerate) (PHVA), poly(p-dioxanone) (PDS), poly(ortho esters), tyrosine-derived polycarbonates, polypeptides and copolymers of the above.

The fibers in the implant material of this invention are preferably oriented predominantly parallel to each other, meaning that greater than fifty percent of the total length of the totality of the fibers, and preferably greater than 75%, are oriented in the same direction or within about 20 degrees, more preferably within about 15 degrees, of the same direction. Preferably, at least as great a portion of the total length of the fibers are oriented as close to parallel to each other as depicted in FIG. 1, a scanning electron micrograph showing a material of this invention.

The material of this invention is preferably porous. The pores are preferably interconnected to allow cell migration and extracellular matrix continuity. Interconnectivity here is defined as substantial physical continuity of porous space throughout the scaffold. The presence of fibers during the foaming stage of the manufacturing process helps to insure a minimum of closed-cell pores, which in turn, maximizes the number of open cells, a measure of the interconnectivity. It is preferred that pore distribution and size be substantially uniform. FIGS. 7A and 7B graph pore size distribution in implant materials without fibers in FIG. 7A and with fibers in FIG. 7B. Significant improvement in uniformity of pore distribution is shown in FIG. 7B with its narrow distribution peak compared to that of FIG. 7A. Uniformity of pore distribution in a fiber-reinforced material of this invention is defined herein as giving rise to a distribution curve showing significantly more uniformity than the distribution curve of the same material without fibers. Fibers help to insure that pore size is uniform by providing well-distributed nucleation sites during the foaming process. It is preferred that the pores have average linear dimensions (distance between pore walls, also referred to herein as "diameter") large enough to accommodate ingrowing cells, e.g., at least about 25 µm, and less than about 300 µm, more preferably between about 50 and about 250 µm.

Alignment of the fibers prior to foaming can lead to preferential alignment of the pores formed during the foaming process. In an embodiment, the pores are substantially aligned with the fibers. In an embodiment, both the pores and the fibers are aligned along one axis of the implant, which can produce higher fluid flow rates along that axis. In an embodiment, the pores and fibers are aligned with an axis which is aligned with the primary direction of loading of the implant after its placement in a defect in a load bearing tissue. Increasing amounts of fibers can lead to greater alignment of the pores.

The porosity (pore volume) of the scaffold is preferably between about 50% and about 80%, and more preferably between about 60% and about 70%. Ideally, the scaffold should be sufficiently porous to facilitate tissue regeneration but not so porous as to compromise its mechanical integrity. The oriented fiber-reinforced material has a characteristic columnar architecture which is "biomimetic" of the columnar cell orientation of chondrocytes in articular cartilage.

The porous material of this invention may be used as a tissue scaffold in vivo or in vitro. That is, the material acts as a scaffold (framework) providing support and spaces for ingrowth of cells either after it has been placed within a tissue defect in the patient's body, or alternatively, the scaffold material of this invention may be preseeded with autologous or allogenic cells or cell-containing media before implantation. By adding cells to the scaffold ex vivo before implantation, the formation of the desired tissue or organ type can be accelerated. For example, addition of bone marrow to the implant accelerates the formation of bone throughout the scaffold due the presence of osteoprogenitor and angiogenic cells. Addition of hepatocytes to a scaffold material has been reported to form liver tissue; similarly, addition of chondrocytes has been reported to form cartilage.

Cells can be pre-treated with growth and differentiation factors to induce proliferation or a desired phenotype.

The scaffold material of this invention can also be pre-seeded with autologous or allogenic tissue. The autologous or allogenic tissue may be minced or particulated. In an embodiment, the tissue is dermal tissue, cartilage, ligament, tendon, or bone. These allogenic tissues can be processed to preserve the biological structure and composition, but remove cells which may cause an immune response. Similarly, autologous tissues can be utilized and processed as described for allografts.

The implants of this invention may be used to deliver bioactive agents such as growth factors, antibiotics, hormones, steroids, anti-inflammatory agents and anesthetics in timed manner, such as in a timed burst or a controlled-release pattern.

The implant material of this invention may be used as one phase of a multiphase implant, e.g. as described in U.S. Pat. No. 5,607,474, incorporated herein by reference to the extent not inconsistent herewith. Preferably, the implant material of this invention has mechanical properties similar or identical to those of the tissue into which the implant is to be placed, controlled by the amount and type of fibers used. The effect of fiber content on mechanical properties is shown in FIGS. 3-6.

Methods of making implant materials are also provided herein. A method for making a fiber-reinforced, porous, biodegradable tissue scaffold implant material comprising fibers aligned predominantly in one direction comprises:
   a) dissolving a biodegradable polymer in a suitable organic solvent to form a solution;
   b) dispersing the fibers in a suitable non-solvent for the polymer to form a suspension.
   c) precipitating the polymer mixed with fibers as a coherent mass from solution by mixing the suspension and solution;
   d) kneading and rolling the coherent mass of fibers and polymer to orient the fibers predominantly parallel to each other; and
   e) applying heat and vacuum pressure to the mass to foam and cure it.

Methods for the preparation of precipitated polymers are well-known to the art. In general, the process comprises mixing a dried polymer mix with a solvent, preferably acetone, precipitating the polymer mass from solution with a non-solvent, e.g. ethanol, methanol, ether or water, extracting solvent and precipitating agent from the mass until it is a coherent mass which can be pressed into a mold or extruded into a mold, and curing the composition to the desired shape and stiffness. Kneading and rolling may be performed as described in PCT Publication WO 97/13533, incorporated herein by reference to the extent not inconsistent herewith. The kneading may be done by hand or machine and should be continued until the fibers are predominantly aligned substantially parallel to each other, e.g. until the mass becomes difficult to work. Kneading and rolling should be stopped just short of the point where the mass becomes too hard to press into the mold. If it is desired to align the fibers in a single plane, the mass should be rolled out for placement in a flat, shallow mold. If it is additionally desired to align the fibers in a single direction, the mass should additionally be stretched in the desired direction of alignment. Placement in a cylindrical mold is preferred when fiber alignment in a single direction is desired, with molds having a length to diameter ratio of about 1 to 10 being preferred. Increasing degrees of parallel fiber orientation can be achieved (up to a limit) by increasing the length to diameter ratio. Curing and foaming the polymer in the mold to form a porous implant may then be done.

If inorganic particles are to be added to the implant, they may be added to the material prior to foaming. In an embodiment, the inorganic particles are added after the dissolution of the polymer in the solvent. In an embodiment, the inorganic particles are added after dispersion of the fibers in the polymer solution.

After the fibers have been dispersed in the porous scaffold, the scaffold may optionally be pressed, e.g., compression molded, preferably at elevated temperatures until all the pores have been collapsed into a fully dense (non-porous) composite. This approach is especially effective in creating a fiber reinforced composite in which fibers are evenly dispersed and results in good interfacial bonding between the fibers and the matrix.

The temperatures required for pressing are as known to the art, those at which the material softens sufficiently to allow intermingling of the polymer chains and collapse of the pores under the pressure being applied. The time and temperature used for compression molding should be sufficient to ensure that no significant residual stresses are present (i.e., the material does not expand when the pressure is released. Using an amorphous PGA (75:25), for example, a temperature of about 100° C. is used. For semi-crystallizing polymers such as L-PLA, a temperature of at least about 180° C. is required.

DETAILED DESCRIPTION

Figure 1:
FIG. 1 is a scanning electron micrograph of a porous, fiber-reinforced biodegradable scaffold implant material showing predominantly parallel orientation of fibers and a characteristic columnar pore architecture.
Figure 2A:
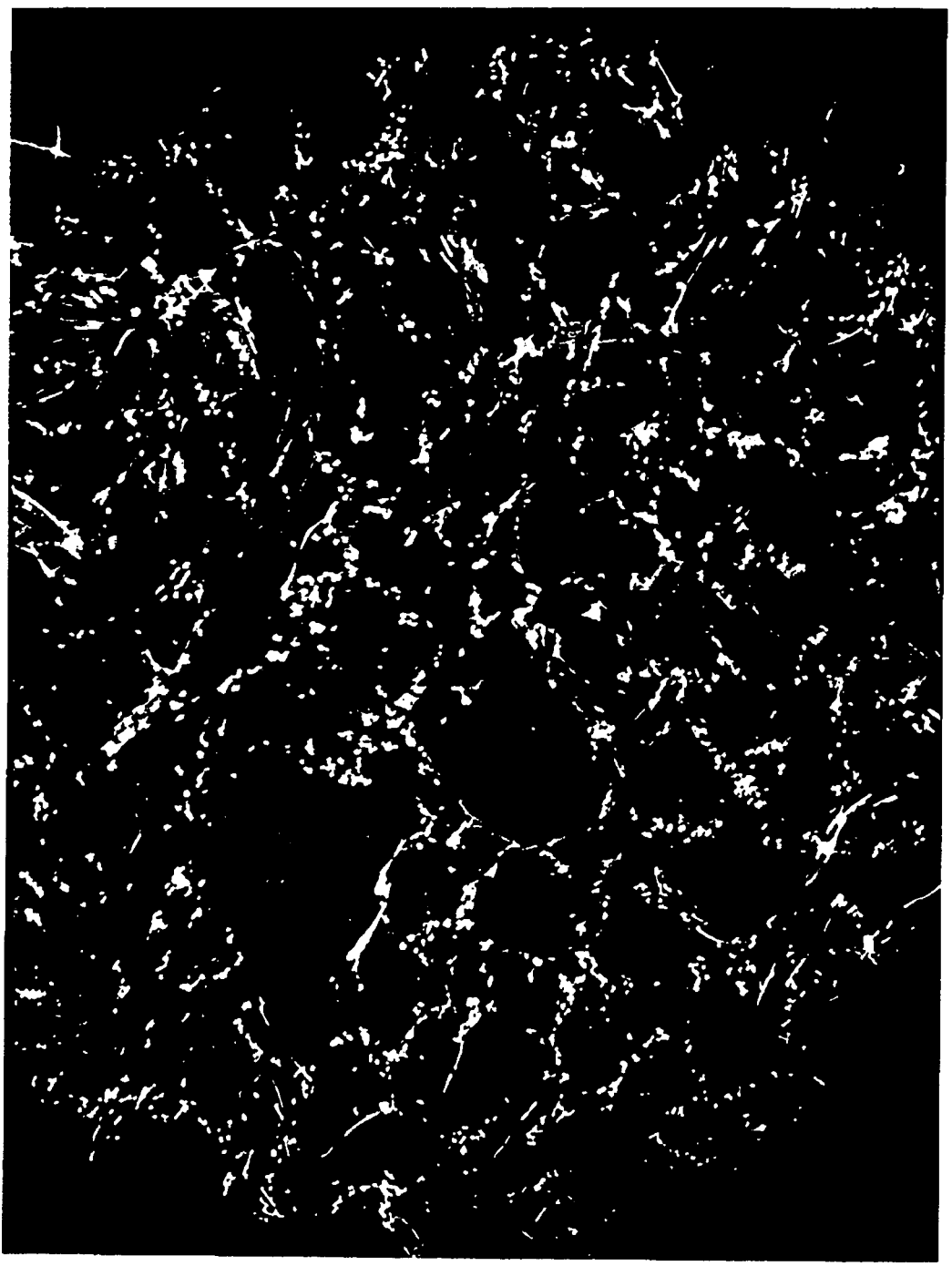
FIGS. 2A and 2B show two cross-sections of a porous, fiber-reinforced implant viewed using a polarized light microscope (A) end-on, viewed parallel to the predominant orientation of the fibers and (B) side, viewed perpendicular to the predominant orientation of the fibers. The fibers appear bright due to their birefringent properties.
Figure 2B:
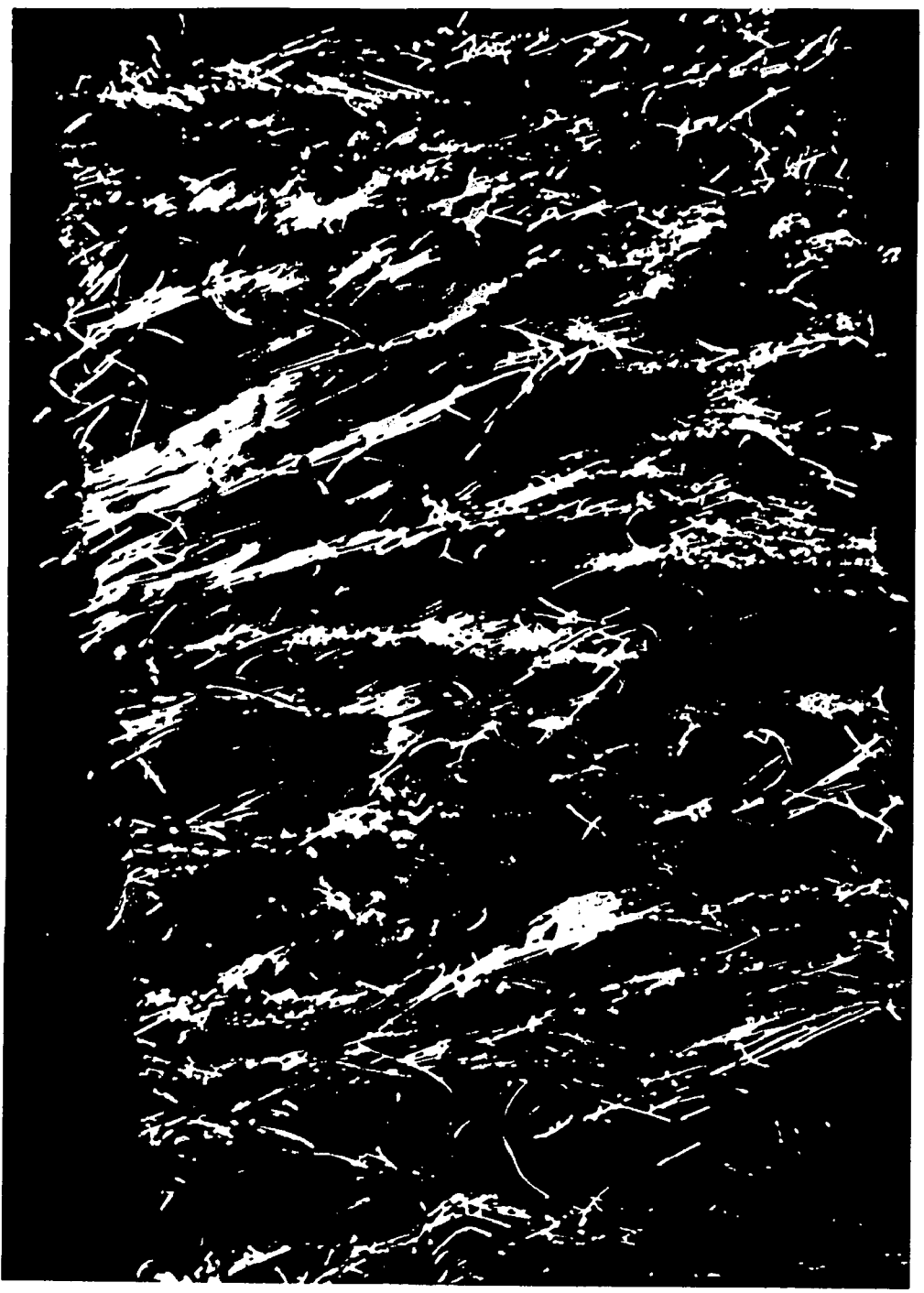

A fiber-reinforced implant material is provided in which the fibers are aligned predominantly parallel to each other. Alternatively, fibers may be aligned in a single plane. The implant material is preferably porous as shown in FIGS. 1 and 2. Alternatively, it may be fully dense (non-porous). Porous implants are useful as tissue scaffolds for tissue ingrowth, and are preferably biodegradable. Non-porous implants may be non-biodegradable and used as permanent implants.

The implant described herein may be used to deliver bioactive agents such as growth factors, antibiotics, hormones, steroids, anti-inflammatory agents, and anesthetics. Bioactive agents further include autologous and synthetic bioactive agents. Autologous bioactive agents include, but are not limited to, concentrated blood, such as Platelet-Rich Plasma (PRP) and Autologous Growth Factor (AGF), and the patient's own bone marrow. Synthetic bioactive agents, include, but are not limited to, bone morphogenic proteins (e.g. BMP-2), peptides growth factors, etc.

Such agents can be adsorbed onto the implant after manufacture or just prior to implantation, delivered in a controlled manner by secondary vehicles incorporated into the implant, or incorporated into the matrix directly. For an immediate bolus release, the implant can be coated by simply applying the agent to the implant in an appropriate vehicle. One example would be dripping a solution containing the agent over the surface of the implant or allowing the implant to soak in the solution for a short time. Upon implantation, a growth factor release pattern provided by this type of treated scaffold can induce an initial rapid proliferation of cells to fill the space within the porous scaffold.

Encapsulation methods for such bioactive agents are generally well described in the art, and these methods can be used for preparing materials for incorporation into the present implant device. Hollow fibers known to the art can be used as reinforcing fibers herein and filled with various bioactive agents as taught by Schakenraad et al. (1988), "Biodegradable hollow fibers for the controlled release of drugs," *Biomaterials* 9:116-120; and Greidanus et al., U.S. Pat. No. 4,965,128, both of which are incorporated herein by reference to the extent not inconsistent herewith. The hollow fibers can additionally aid in providing channels for cell/tissue infiltration. This serves the dual purpose of providing the requisite mechanical properties to the implant and delivering the bioactive agent.

A variety of polymer compositions can be employed to give varying mass degradation rates as well as varying bioactive agent delivery rates. The bioactive agent can be delivered in a controlled manner to achieve a desired period of release or release at a specific point in time. The bioactive agent can be incorporated into the matrix directly during manufacture, as is described by Athanasiou et al. in U.S. patent application Ser. No. 08/452,796, "Continuous Release Polymeric Implant Carrier," which achieves a continuous release of the factor over a specified time. Alternatively, encapsulation via one of the many techniques known in the art can be used. By appropriate selection of polymer and encapsulation method, release can be achieved over a very broad range of times, from virtually immediate release to delayed release of up to 6 months. A delayed release could be desirable for delivering appropriate factors at different times during the healing process. For example, in a cartilage repair model, a proliferation factor such as PDGF-BB can be delivered quickly to the defect site and then, when a sufficient population of cells are present in the scaffold, a differentiation factor such as TGF-β to induce the formation of type II collagen can be delivered.

As described above, the implant may be preseeded with autologous or allogenic cells prior to implantation. There are a number of techniques for adding cells to scaffolds. In the present invention, cells can be loaded by immersing the implant materials in a suspension of cells and gently agitating for about 2 hours. Cells infiltrate the scaffold, adhere to the polymer matrix, and go on to proliferate and differentiate. Alternatively, a vacuum-loading method can be used, in which the implant is immersed in a suspension of cells and a gentle vacuum (about 300 mm Hg) is slowly applied. It is important to apply vacuum slowly so that excessive shear forces and cell lysis are avoided within the implant. Yet another cell-loading technique is to infiltrate the scaffold material by centrifugation. The implant is fixed in the bottom of a small centrifuge or microfuge tube and a suspension of cells added. The implant/cell combination is then spun at 200-1000×G for 5 to 15 minutes. Excess solution is decanted and the loaded implant may be removed for immediate implantation or incubated for a short-term culture period before implantation into the patient. Cells used for implant seeding can be acquired in a number of ways. They can be isolated from autograft tissue, cultured and expanded from autograft tissue, or derived from donor allograft tissues.

Chopped or micronized tissues can be loaded onto the scaffold by similar methods. Tissue particles can be loaded by immersing the implant materials in a suspension of the tissue particles and gently agitating for about 2 hours. Alternatively, a vacuum-loading method can be used, in which the implant is again immersed in a suspension of tissue and a vacuum is applied. Yet another loading technique is to infiltrate the scaffold material by centrifugation. The implant is fixed in the bottom of a centrifuge or microfuge tube and a suspension of tissue particles added. The implant/cell combination is then spun at 200-1000×G for 5 to 15 minutes. Excess solution is decanted and the loaded implant removed for implantation into the patient. For clinical ease of use, a double syringe system is set u whereby the tissue suspension can be forced back and forth between the syringe barrels to infiltrate the scaffold completely. Loading methods that can be done aseptically in an operating room setting are preferable.

When the fiber-reinforced scaffold is used for articular cartilage regeneration, the fiber and matrix combination is preferably selected such that the mechanical properties of the composite scaffold are tailored to optimal performance for use in an articular cartilage environment. Optimal performance may be determined based on the mechanical properties of the scaffold tested under physiological conditions immediately after wetting and after being immersed in vitro in physiological solution, i.e., phosphate buffered saline, synovial fluid, etc., or in vivo for critical time periods. For articular cartilage repair, it is preferred that, after 2 weeks of immersion in vitro, the compressive Young's modulus of the scaffold be within about 50% of that of articular cartilage tested under identical simulated physiological conditions and testing modality. Simulated physiological conditions include at least an aqueous environment maintained at 37° C. It is preferred that the yield strength of the scaffold be at least about 1 MPa, more preferably at least about 2 MPa, after two weeks of immersion and testing under said conditions. Such a yield strength gives the scaffold sufficient mechanical integrity to withstand the stresses experienced during normal human gait. Furthermore, it is preferred that the scaffold maintain at least 50% of its yield strength, tested under said conditions, after two weeks of immersion time.

The mass degradation rate of the scaffold is also a property which may be tailored for optimal performance. As known to the art, mass degradation rate may be controlled by type of biodegradable polymer, molecular weight, and degree of crystallinity (for semi-crystalline polymers). For repair of articular cartilage, it is preferred that at least about 90% of the scaffold be resorbed by between about eight weeks and about 26 weeks after implantation. For bone repair, it is preferred that at least about 90% of the scaffold be resorbed between about ten weeks and about 16 weeks, but by no more than about 26 weeks after implantation.

To make the fiber-reinforced scaffolds of this invention, the reinforcing fibers and matrix polymer are selected as described above. The matrix polymer is dissolved in an appropriate amount of solvent such that the viscosity of the completely dissolved solution is roughly similar to that of motor oil (50-500 centipoise). The reinforcing fibers are immersed in a non-solvent of the polymer. The fibers are left to soak in the non-solvent for at least 15 minutes so that the non-solvent will wet the fibers as much as possible. After letting the fibers soak, they are mixed or blended into a slurry with the non-solvent to disperse the fibers and remove any clumping. It is preferred that extra non-solvent be added to the slurry during blending or mixing. Blending or mixing should be carried out until there are no visible dense clumps of fibers within the slurry. After blending or mixing, the non-solvent is decanted so that only the amount of non-solvent needed for precipitation of the polymer (at least about 90% of the dissolved polymer is desirably precipitated) remains.

Once the matrix polymer is completely dissolved and the fibers are well dispersed in the non-solvent, the two are added together and stirred, preferably with a non-stick utensil. Stirring should be continued until an opaque, cohesive gel has precipitated and can be lifted out onto a non-stick surface. The gel is then kneaded to disperse the fibers uniformly within the gel. Uniform dispersion can be assessed by visual observation of the gel when flattened. The gel is kneaded until the fibers are uniformly dispersed and most of the supernatant solvent and non-solvent has been squeezed out. A non-stick roller is then used to flatten the gel on the non-stick surface.

An initial vacuum foaming step is then performed to remove more of the residual solvent and non-solvent and to initiate the nucleation of air bubbles in the gel. A vacuum pressure of about 700 mm Hg (60 mm absolute) is preferably pulled on the gel for about 1 to 2 minutes. Following this vacuum step, the gel is fed through rollers separated by a gap of preferably about 0.25 to 0.75 mm for a sufficient number of times that the gel dries further and becomes tough to knead.

At this point, the gel is shaped according to the type of mold being used; the type of mold to use depends on the type of orientation of the fibers desired. If one desires the fibers to be substantially aligned in one direction, the mold used should have a cylindrical shape with a length to diameter ratio of at least about 5:1. The gel is rolled to the length of the cylindrical mold and then placed within the mold. If one desires the fibers to be substantially aligned in one plane, the mold should be a parallelepiped having a maximum ratio of about 1:5 between the smallest dimension and each of the other two dimensions, or cylindrical with a length to diameter ratio of at most 1:5. The gel is flattened using a non-stick rolling pin to fill the largest two dimensions of the parallelepiped mold or the circumference of the cylindrical mold.

Following kneading, the rolled or flattened gel is placed into its mold, and the mold is closed and placed into a vacuum oven. In this second vacuum foaming step, the vacuum pressure should reach at least about 700 mm Hg and the temperature should be set sufficiently high as to remove residual solvent from the gel but not so high as to cause significant coalescence of pores during curing, e.g. about 65° C. During this step, the gel foams and expands to the walls of the mold and enough of the residual solvent and non-solvent is extracted so the porous composite can be removed from the mold without deformation of the composite. The length of time for the second vacuum step is typically about one day, but two or three days may be necessary for successful results. Following removal of the composite from the mold, a sample of the composite should be analyzed for residual solvent and non-solvent levels. Subsequent drying of the composite outside of the mold may be necessary, as the residual levels should be no more than 100 ppm. The composite may then be cut to its desired shape and orientation depending on the type of application for which it will be used.

Scaffolds of the present invention can be used in the treatment of partial thickness, full thickness and osteochondral cartilage defects. A partial thickness defect is defined as one in which the depth of the defect is only a portion of the entire thickness of the cartilage layer. A full thickness defect is defined as one in which the defect penetrates through the entire thickness of cartilage, but does not extend into the underlying subchondral bone. An osteochondral defect penetrates both the cartilage and the bone. In some instances, it may be desirable to treat a cartilage defect with a multiphase implant which protrudes into the subchondral bone. A multiphase implant is defined as an implant device which consists of one or more layers. This device may include a solid film, a cartilage phase, a bone phase, etc.

To treat a full thickness defect, the invention is preferably used as a single phase implant thick enough to fill the defect. For example for humans, an implant 8 mm in diameter with a thickness of 2.0 mm might be a typical size. The implant will preferably have a biodegradable film covering the articulating surface of the implant to allow for a smooth surface during articulation; however, this film is not a requirement. The implant is then preferably loaded with a suspension of autologous cells isolated from an articular, costochondral, perichondrial, or any other hyaline cartilage donor site. After isolation of the cells from the tissue, they can be expanded in culture, pre-treated with growth factors, hormones, or other biologically active molecules, or they can be used neat without further treatment. Once the cell suspension is prepared, the cells can be loaded onto the implant.

To prepare the implant, the sterile scaffold is added to the prepared cell suspension, using just enough media for the cell suspension to cover the implant. The cell/scaffold combination is then shaken gently in an orbital shaker for 1-2 hours to infiltrate the porous material with cells. The implant, wetted with media, is then removed and transferred to the surgical site, maintaining the implant at 37° C. to assure the viability of the cells. Alternatively, the scaffold/cell combination can be maintained under culture conditions for an extended period of time to allow the cells to attach or even to begin to proliferate and form extracellular matrix.

To treat a full thickness defect on the femoral condyle, for example, the surgeon preferably exposes the femoral condyle of the affected knee and uses a circular boring tool to cut a "ring" around the damaged site. Using a curette or other appropriate tool, the surgeon then removes all of the damaged cartilage. Once the defect site is prepared, a small amount of fibrin glue or other bio-compatible tissue adhesive is applied to the bottom of the defect site. In selecting the adhesive, it is important to ensure compatibility with the implant materials. The prepared implant is then press fit into the defect site until the surface of the implant is flush with the surface of the cartilage, using the tissue adhesive to secure the implant in place. Alternatively, the prepared implant can be mechanically attached into the defect site using sutures, anchors, rivets, microscrews, tacks, etc., all of which can be made from a biodegradable material. The site is then closed routinely and the appropriate post-surgical therapy prescribed. Continuous passive motion, electrical stimulation, or other treatment can be used as deemed appropriate; however, weight bearing on the treated leg should be avoided or minimized for at least the first 4 to 6 weeks. Repair should be nearly complete within 12 weeks, with complete recovery expected in 4 to 6 months. Optimal post-operative treatment/rehabilitation regime can be determined by the surgeon/physician.

EXAMPLE 1

Method of Producing a 10% Chopped PGA Fiber-Reinforced, Porous, Biodegradable Implant To manufacture a 70 volume % porous, 10 volume % chopped PGA fiber-reinforced, 75:25 poly(D,L-lactide-co-glycolide) (D,L-PLG) wafer, the following procedure was used. First, 1.38 g of 75:25 D,L-PLG (Mw=95,000 Da, intrinsic viscosity=0.76) was dissolved in a Teflon beaker using 6.2 mL of acetone. Next, 0.153 g of PGA fibers with a diameter of approximately 15 cm, chopped to an average length of about 2.6 mm, were placed in a scintillation vial. Then, 6.2 mL of ethanol was added to the vial with the fibers. The level of fluid in the vial was marked with a permanent marker. Next, the fibers and ethanol were transferred to a Waring blender with an additional 20 mL of ethanol. The mixture was blended on setting 2 for a period of 1 minute. The fiber and ethanol mixture was then added back into the scintillation vial, and the ethanol was decanted until the height of the mixture decreased to the marker.

After the 75:25 D,L-PLG was completely dissolved in the acetone, the fiber and ethanol mixture was poured into the polymer solution and mixed with a Teflon policeman. The solution was mixed until a cohesive gel of precipitated polymer and fiber mass had formed. The gel was then removed from the supernatant acetone and ethanol. Next, the gel was kneaded by hand, taking particular care to manually disperse the fibers within the composite gel. When the gel became somewhat dry and the fibers appeared well distributed upon macroscopic observation, it was processed nine times through rollers separated by a distance of about 0.25 mm. Next, the gel was rolled by hand into a cylindrical shape with a length equal to the length of the mold, which was 5 cm. The gel was then placed in the cylindrical polypropylene mold with a 1 cm diameter and a 5 cm length. During this rolling process, the chopped fibers in the gel became preferentially oriented in the longitudinal direction of the cylinder. The mold was then placed in a vacuum oven preheated to a temperature of 65° C. and a vacuum was drawn to at least 700 mmHg. After one day in the mold in the vacuum oven, the gel had foamed to the size of the mold and had dried to a stiff, structural porous composite. It was then put back in the vacuum oven, open, to remove residual acetone and ethanol, for at least three days.

After the dried, porous composites were removed from the vacuum oven and before any other characterization and use, the residual amount of acetone and ethanol from a portion of the composite was measured using gas chromatography. Subsequent reinsertion into the vacuum oven at 65° C. was done until the residual solvent levels fell below 100 ppm.

To process the cylindrical wafer into the desired shapes and sizes, the following procedures were used. The cylindrical wafer was mounted on a Buehler Isomet 1000 Saw and cut transversely to the desired cylindrical height using a diamond-coated saw blade with water as a coolant. The chopped cylinders were then sized to the desired diameter using a hollow coring tool mounted on a drill press.

EXAMPLE 2

Mechanical Testing to Show the Influence of Fiber Orientation on the Mechanical Properties of Porous, Biodegradable Implants To make porous wafers with reinforcing fibers oriented preferentially in one direction, the manufacturing method described in the detailed description of the preferred embodiments and Example 1 was used. The addition "cyl" is attached to those implants made using this method, to indicate the cylindrical molds that were used. To make implants with reinforcing fibers oriented in two directions, a plate-like mold was used with dimensions 6 cm×6 cm×3 mm thick and the gel was flattened to fit the sides of the mold before the final vacuum step. The addition "flat" is attached to the implants made using this method, and indicates the flat, plate-like form of the cured wafer.

The matrix polymer used was a random copolymer of 75:25 poly(D,L-lactide-co-glycolide) and the fibers were poly(glycolide) with a diameter of about 15 µm and an average length of about 2.5 mm. The dimensions of the samples used for mechanical testing were 6 mm diameter by 3 mm height, obtained using the methods described in Example 1.

The method used to measure the mechanical properties of the cylindrical wafers was an unconfined parallel plate compression test. The apparatus consisted of a calibrated Instron Model 5542 Load Frame and Instron 500N capacity tension-compression load cell equipped with an environmental bath, loaded with deionized water and capable of maintaining a temperature of 37° C. Cylindrical samples mentioned above were preloaded with deionized water by pulling a vacuum on the immersed samples and were preconditioned in deionized water for one hour prior to testing in an oven maintained at 37° C. Before testing, each sample was removed from the oven, measured using calipers to determine thickness and diameter, and immediately immersed in the bath between unconfined parallel compression platens. The samples were then compressed at a strain rate of 10% per minute and the stress versus strain data obtained from the test were collected and analyzed according to ASTM D 1621-94, "Standard Test Method for Compressive Properties of Rigid Cellular Plastics."

Samples were tested either parallel (∥) or perpendicular (⊥) to the preferred orientation of the fibers. Implants without fiber reinforcement were made and tested in the same configurations as those with fiber reinforcement. The parallel or perpendicular description for these implants indicates that samples were made and tested in the same configuration as the corresponding fiber-reinforced implant. Five groups of samples were manufactured and tested according to the following descriptions:
1. 75:25 D,L-PLG (w/o fibers), flat, ⊥
2. 75:25 D,L-PLG (w/o fibers), cyl, ∥
3 10% PGA fibers/90% 75:25 D,L-PLG, flat, ⊥
4. 10% PGA fibers/90% 75:25 D,L-PLG, cyl, ∥
5. 10% PGA fibers/90% 75:25 D,L-PLG, cyl, ⊥
From the stress versus strain data and postprocessing analysis, the Young's modulus and yield stress of the samples were compared. This was correlated with the porosity of the samples, calculated from the dry mass, thickness, and diameter of the cylindrical samples and density of the polymers used. A composite plot of the Young's modulus and porosity of each of the implants is given in FIG. 3. A plot of the yield stress of each of the implants is given in FIG. 4.

Figure 3:
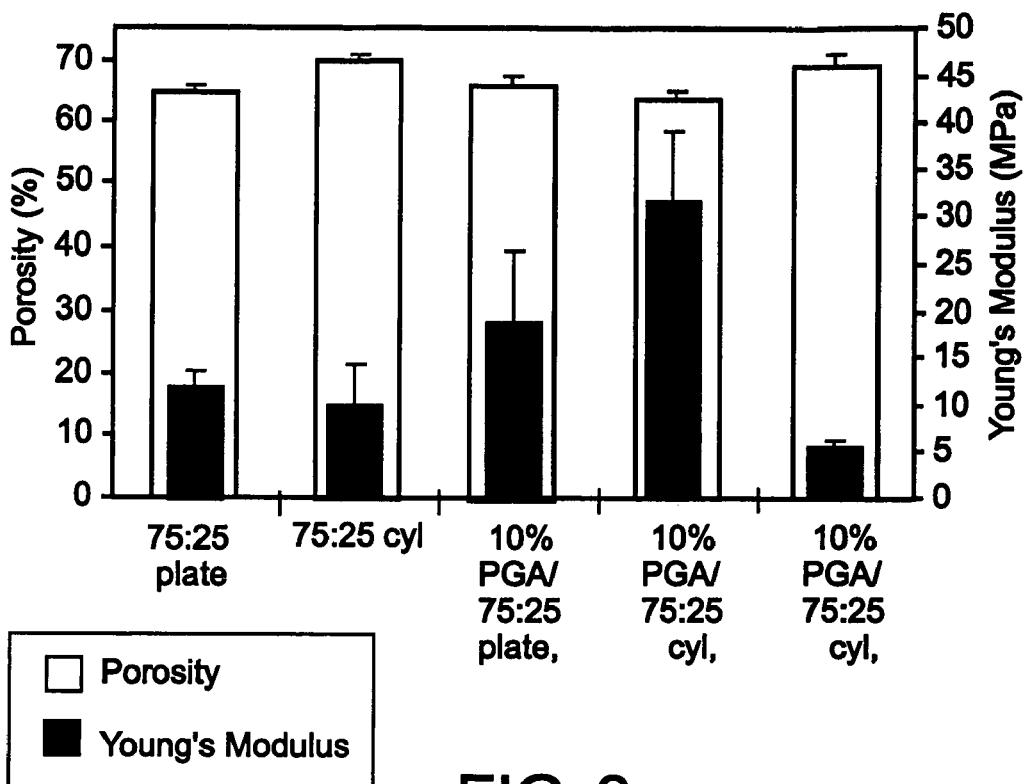
FIG. 3 is a composite plot of Young's modulus and porosity of implant materials of this invention composed of PGA fibers reinforcing 75:25 polylactide:glycolide. The white bars indicate porosity. The black bars indicate Young's modulus. The term "plate" designates materials made by a process in which fibers are predominantly aligned in a single plane. The term "cyl" designates materials made by a process in which fibers are predominantly aligned in a single direction. The percent designation indicates percentage of fibers present. When this percent designation is absent, the materials were made by the process indicated by "plate" or "cyl" with no fibers present.
Figure 4:
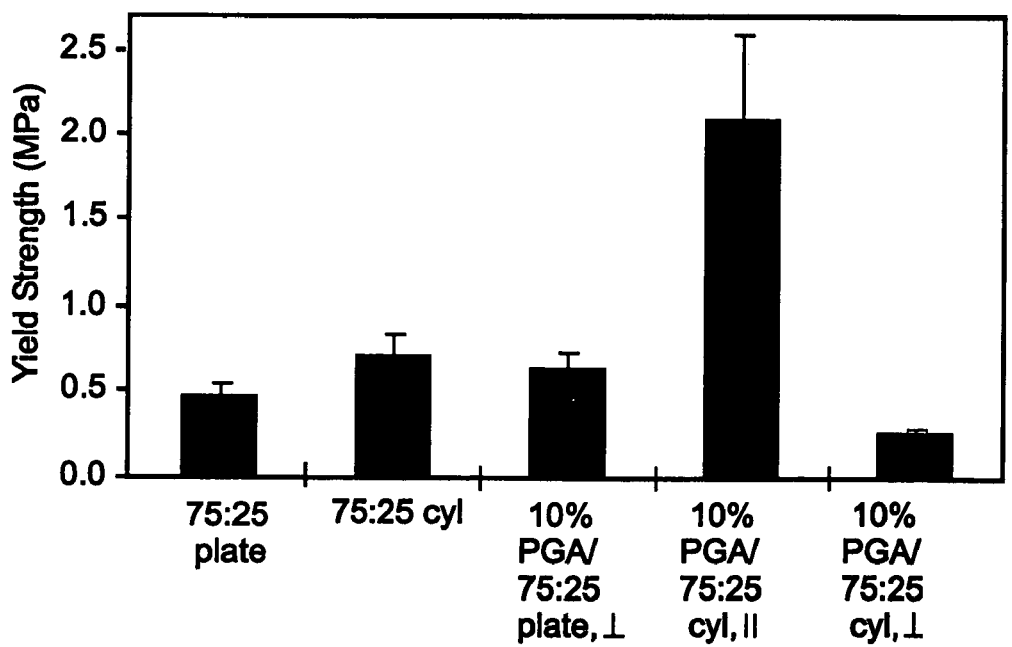
FIG. 4 is a plot of the yield stress of the implant materials shown in FIG. 3.

FIG. 3 shows that a porosity of 60% to 70% was maintained for all implants tested. FIGS. 3 and 4 show, first of all, that without fiber reinforcement, the manufacturing method did not influence the Young's modulus of the implants, and only slightly changed the yield stress. Secondly, FIGS. 3 and 4 show that preferential orientation of the fibers in the reinforced implants caused a much larger increase in the Young's modulus and yield strength when tested parallel to the direction of preferential orientation. Furthermore, when the implants were made in the plate-like mold, addition of reinforcing fibers only mildly increased the Young's modulus and did not significantly change the yield strength when tested perpendicular to the preferential orientation of the fibers. FIGS. 3 and 4 also show that the fiber-reinforced implants made in the cylindrical mold have anisotropic mechanical properties; the Young's modulus and yield strength were much greater when tested parallel to the direction of preferential orientation of the reinforcing fibers.

EXAMPLE 3

Mechanical Testing to Show the Influence of Increasing Levels of Chopped PGA Fiber-Reinforcement on Porous, Biodegradable Implants Implants were made according to the method described in the detailed description of embodiments and in Example 1. The matrix polymer used was a random copolymer of 75:25 poly(D,L-lactide-co-glycolide) and the fibers were poly(glycolide) with a diameter of about 15 µm and an average length of about 2.5 mm. Implants were made with fiber volume fractions of 0%, 5%, 10%, 15%, and 20%. Cylindrical samples of about 6 mm diameter and 3 mm length were prepared according to the description in Example 1. The parallel plate compression test method described in Example 2 was used to measure the mechanical properties of the cylindrical wafers. The wafers were tested parallel to the direction of preferential orientation of the fibers.

From the stress versus strain data and postprocessing analysis, the Young's modulus and yield stress of the samples were compared. This was correlated with the porosity of the samples, calculated from the dry mass, thickness, and diameter of the cylindrical samples and density of the polymers used. A composite plot of the Young's modulus and porosity of each of the implants is given in FIG. 5. A plot of the yield stress of each of the implants is given in FIG. 6.

Figure 5:
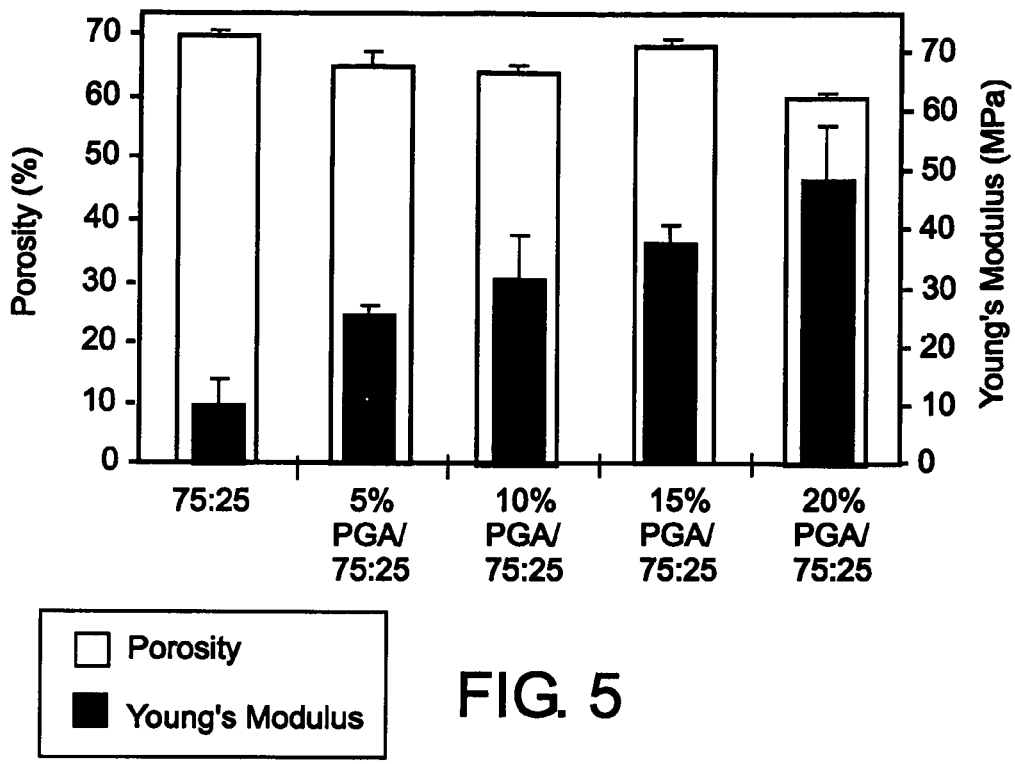
FIG. 5 is a composite plot of the Young's modulus and porosity of implant materials of this invention made with 75:25 polylactide:glycolide and varying percentages of fiber with figure designations as set forth for FIG. 3 above.
Figure 6:
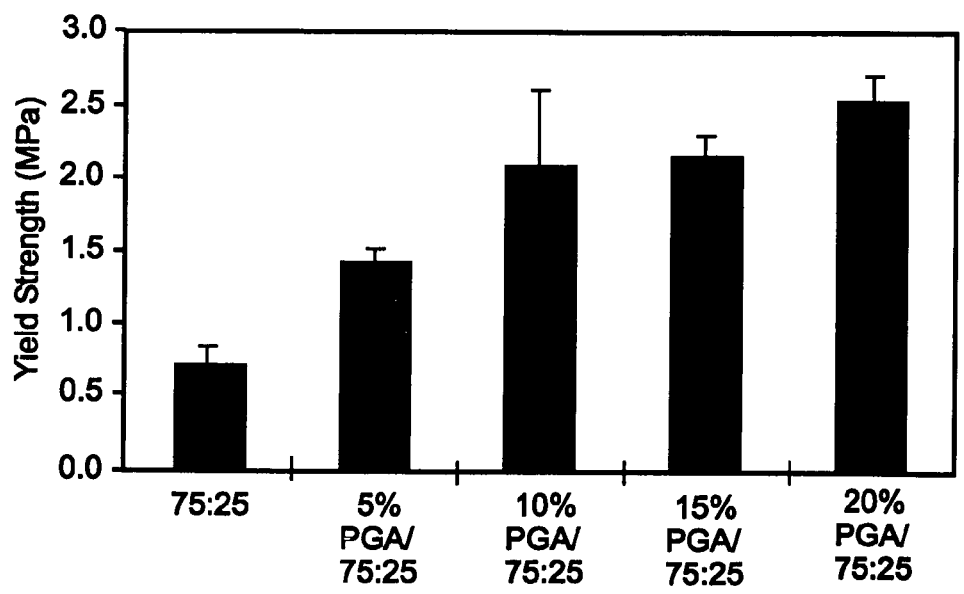
FIG. 6 is a plot of the yield stress of the implant materials shown in FIG. 5.
Figure 7A:
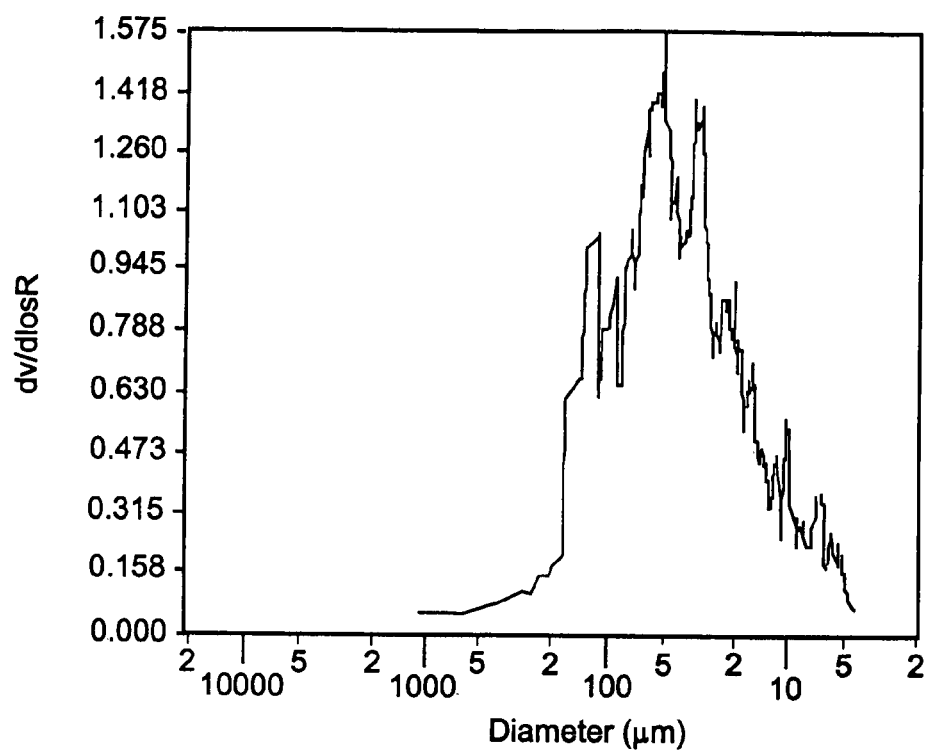
FIGS. 7A and 7B show pore size distribution plots, constructed using mercury porosimetry analysis on porous implants made (A) without fiber reinforcement and (B) with fiber reinforcement. The narrow peak in (B) shows that the fiber-reinforced implant has a more uniform pore size distribution than that without fiber reinforcement (A).
Figure 7B:
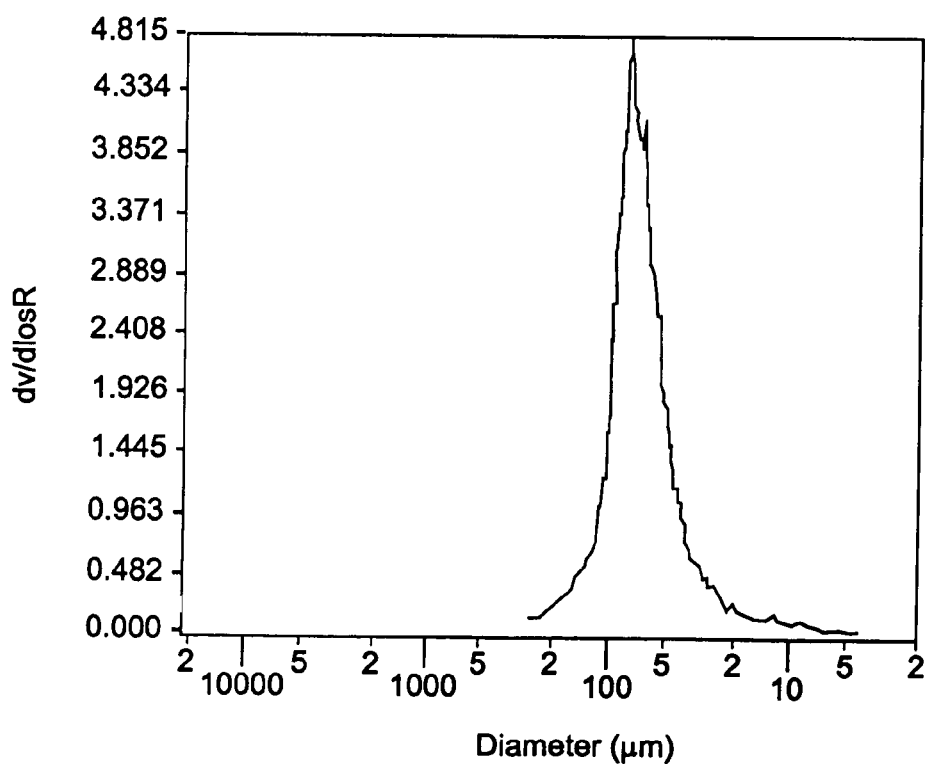

FIG. 5 shows that the Young's modulus increased linearly with increasing addition of reinforcing fibers. FIG. 5 also shows that the porosity of the implants was maintained between 60% and 70%. FIG. 6 shows that the yield strength of the implants also increased with increasing fiber reinforcement.

EXAMPLE 4

Compression Molding of Chopped PGA Fiber Reinforced Composite Material

Fiber-reinforced material was made according to Example 1. This material was then placed into a stainless steel mold, which was then placed between two heated platens in a Carver Laboratory Press. The platens were heated to about 100° C. and a pressure of 10,000 lbs was applied. After about two minutes, the mold was cooled to room temperature and the pressed composite material was removed. The final material was fully dense with a uniform distribution of fibers evidence when held up to light.

EXAMPLE 5

Pore Structure of Porous Resorbable Scaffolds

Figure 8A:
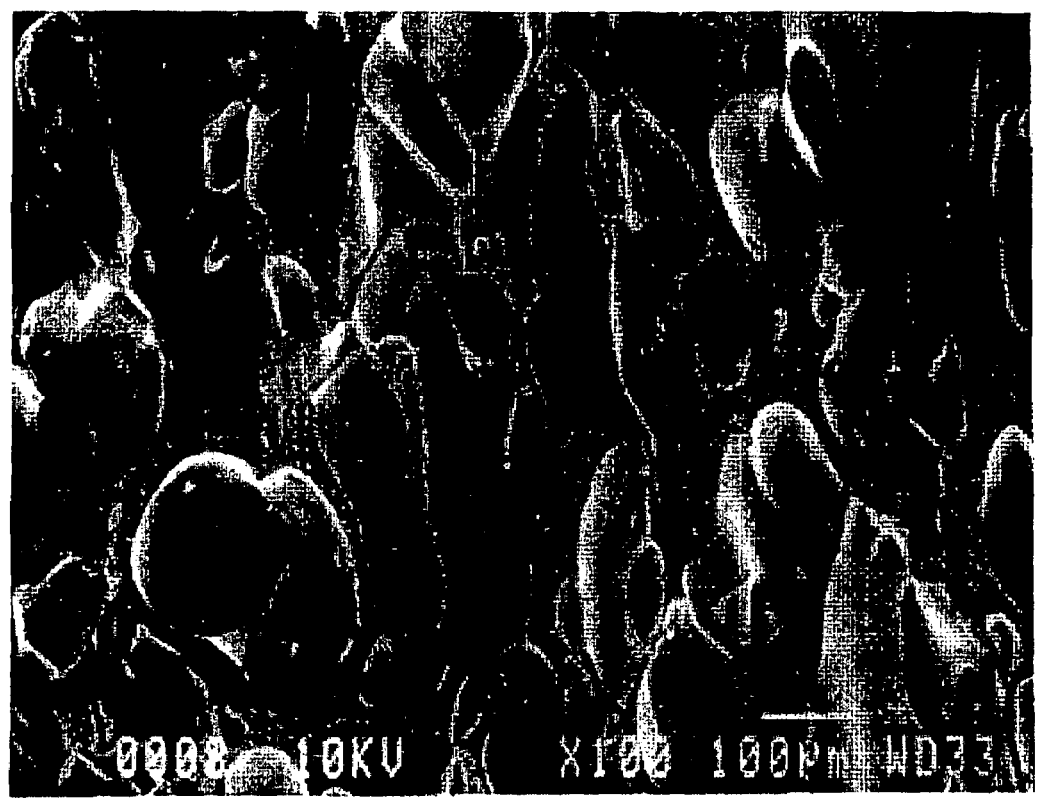
FIGS. 8A through 8D show the pore structure of porous resorbable scaffolds with different amounts of fibers.
Figure 8B:
Figure 8C:
Figure 8D:
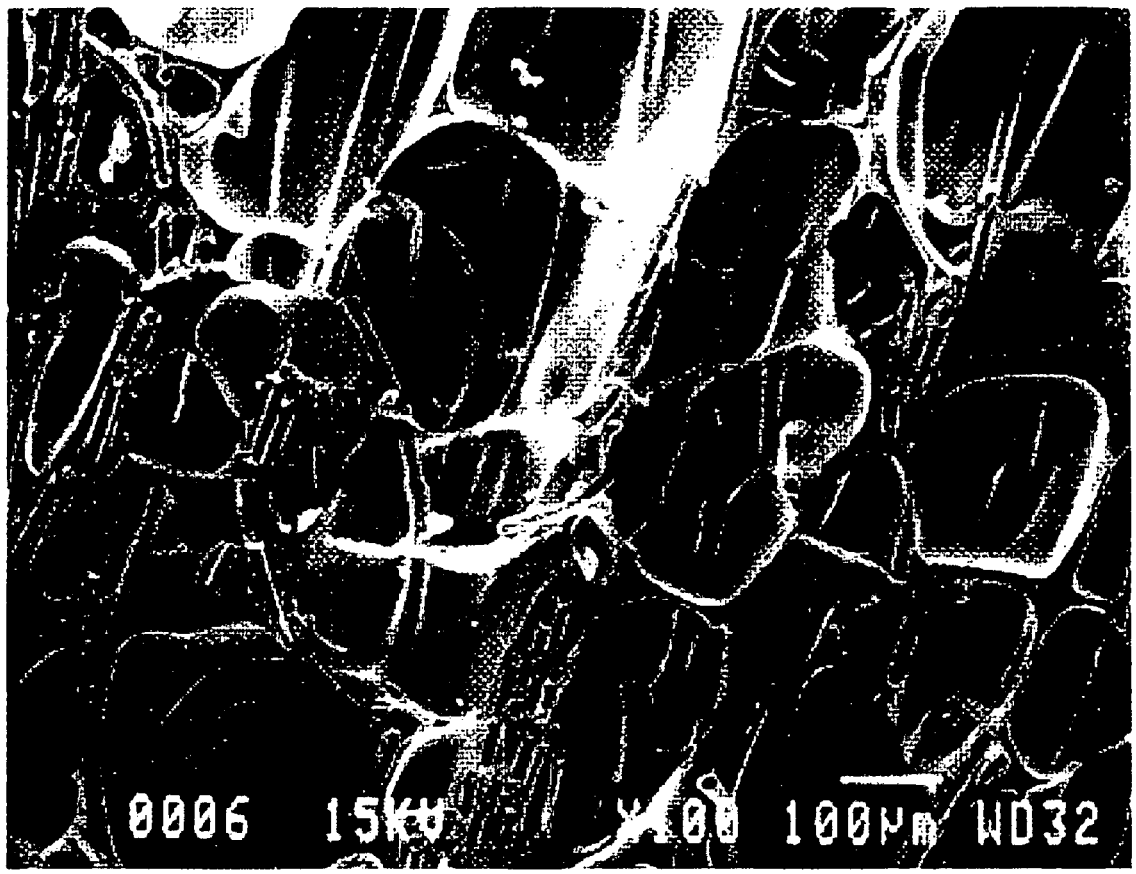

FIGS. 8A through 8D show the pore structure of scaffolds with varying amounts of fibers. Scaffold compositions are as follows: FIG. 8A: 75:25 D,L-PLG neat, FIG. 8B: 5% PGA fiber/75:25 D,L-PLG, FIG. 8C: 10% PGA fiber/75:25 D,L-PLG, and FIG. 8D: 20% PGA fiber/75:25 D,L-PLG. FIGS. 8A-8D show that as the fiber content increases the pores' alignment appears to increase.

EXAMPLE 6

Method of Producing a Fiber-Reinforced, Ceramic-Containing Porous, Biodegradable Implant To prepare a 75% porous material containing 10 vol % fibers, 35 vol % calcium sulfate, and 55 vol % polymer, 2.29 grams of an 85/15 DL-PLG polymer (molecular weight 112 kDa) is dissolved in 10.2 grams of chloroform for 45 minutes. The PGA fibers (15 µm diameter, 2-3 mm long) are rinsed in ethanol and completely dried under vacuum. Once the polymer is completely dissolved, the fibers are thoroughly dispersed in the polymer solution using either hand or mechanical agitation. After the fibers are uniformly dispersed (about 2 minutes mixing time), the calcium sulfate hemihydrate (>98% purity, typical mean particle size=25 µm) is added and mixed to completely incorporate the powdered material, about 2 to 3 minutes.

Once the mixture is substantially uniform, 9.9 grams of 95% ethanol is added in two additions to precipitate the material. The supernatant liquid is decanted and the material turned out on to a Teflon plate. Using chemical resistant gloves, the material is manipulated to remove the excess fluid from the material to form a soft, coherent mass. The material is weighed and divided into two pieces, which are then individually rolled into "ropes", about 6 inches long. The elongated material is folded into thirds and the rolling procedure repeated 3 to 8 more times to align the fibers. Finally, each piece of material is rolled into a length that fits into the well (10 mm diameter by 90 mm long) of a polypropylene mold. The mold is assembled and placed into a vacuum oven at 72° C. and <5 mm pressure (absolute) for 48 hours to fully cure the material. Gas chromatography has shown that the residual solvents after curing are less than 100 ppm.

The resulting materials are fully expanded, white cylinders with an overall porosity of about 75% and a mean pore size of about 250 µm. Each "cigar" of material can be cut to form disks, plugs, or cubes to suit a particular application, or shredded to form irregular porous granules.

Those of ordinary skill in the art will appreciate that alternative techniques, procedures, methods and reagents other than those specifically described in the foregoing examples can be readily employed or substituted to achieve the objects of the present invention, i.e., polymeric fiber-reinforced compositions with fibers aligned in predominantly parallel or planar alignment, and methods for making same. Alternative, but functionally equivalent, compositions and methods will be readily apparent to those of ordinary skill in the art without expense of undue experimentation. All such alternatives, variations and equivalents are to be considered to be encompassed within the spirit and scope of the present invention.

The invention claimed is:

1. A fiber-reinforced, biodegradable, porous implant material comprising a polymeric matrix having biodegradable inorganic particles substantially uniformly distributed therein and having fibers of a length no greater than about one cm substantially uniformly distributed therein in a predominantly parallel orientation, wherein pores of the material are substantially aligned with the fibers and a ratio of the volume of the fibers to a sum of the volume of the polymer forming the polymeric matrix, the volume of the fibers, and the volume of the inorganic particles is between about 5% to about 50%.

2. The implant material of claim 1, where the pore volume of the implant material is between about 50% and about 80%.

3. The implant material of claim 1, wherein the particles are calcium sulfate or a salt of calcium phosphate.

4. The implant material of claim 1, wherein the size of the particles is between about 0.5 and about 2000 microns.

5. The implant material of claim 4, wherein the size of the particles is between about 8 and about 300 microns.

6. The implant material of claim 1 further comprising autologous or allogenic tissue.

7. The implant of claim 6 wherein the autologous or allogenic tissue is minced or particulated.

8. The implant of claim 6 wherein the tissue is dermal tissue, cartilage, ligament, tendon, or bone.

9. The implant of claim 1 further comprising bioactive agents.

10. A fiber-reinforced, biodegradable porous implant material comprising a polymeric matrix having biodegradable inorganic particles substantially uniformly distributed therein and having synthetic fibers of a length no greater than about one cm substantially uniformly distributed therein in a predominantly parallel orientation, wherein pores of the material are substantially aligned with the fibers and a ratio of the volume of the inorganic particles to a sum of the volume of the inorganic particles, the volume of the fibers, and the volume of the polymer forming the polymeric matrix is between about 2% to about 60%.

11. The implant material of claim 10 wherein the implant is a three dimensional structure having an axis with which the pores of the material and the fibers are aligned with, where the axis defines a primary direction of loading of the implant after its placement in a defect in a load bearing tissue.

12. The implant material of claim 1 wherein the implant is a three dimensional structure having an axis with which the pores of the material and the fibers are aligned with, where the axis defines a primary direction of loading of the implant after its placement in a defect in a load bearing tissue.

13. The implant material of claim 10 further comprising autologous or allogenic tissue.

14. The implant of claim 13 wherein the autologous or allogenic tissue is minced or particulated.

15. The implant of claim 13 wherein the tissue is dermal tissue, cartilage, ligament, tendon, or bone.

16. The implant of claim 10 further comprising bioactive agents.

17. A fiber-reinforced, biodegradable, porous implant material comprising a polymeric matrix having biodegradable inorganic particles substantially uniformly distributed therein and having fibers of a length no greater than about one cm substantially uniformly distributed therein in a predominantly parallel orientation, wherein a ratio of the volume of the fibers to a sum of the volume of the polymer forming the polymeric matrix, the volume of the fibers, and the volume of the inorganic particles is between about 5% to about 50% and the implant is a three dimensional structure having an axis with which the pores of the material and the fibers are aligned with, wherein the axis defines a primary direction of loading of the implant after its placement in a defect in a load bearing tissue.

18. A fiber-reinforced, biodegradable, porous implant material comprising a polymeric matrix having biodegradable inorganic particles substantially uniformly distributed therein and having fibers of a length no greater than about one cm substantially uniformly distributed therein in a predominantly parallel orientation, wherein a ratio of the volume of the inorganic particles to a sum of the volume of the polymer forming the polymeric matrix, the volume of the fibers, and the volume of the inorganic particles is between about 2% to about 60% and the implant is a three dimensional structure having an axis with which the pores of the material and the fibers are aligned with, wherein the axis is aligned with the defines a primary direction of loading of the implant after its placement in a defect in a load bearing tissue.

* * * * *

UNITED STATES PATENT AND TRADEMARK OFFICE
CERTIFICATE OF CORRECTION

| | | |
|---|---|---|
| PATENT NO. | : 7,524,335 B2 | Page 1 of 1 |
| APPLICATION NO. | : 10/931474 | |
| DATED | : April 28, 2009 | |
| INVENTOR(S) | : Slivka et al. | |

It is certified that error appears in the above-identified patent and that said Letters Patent is hereby corrected as shown below:

On the Title Page, Item (63)
Under the heading, "Related U.S. Application Data," paragraph number "(60)" 1st occurrence should be changed to (63), line 2, should state . . .which is a division<u>al</u> of application No. 09/426,686, filed as application No. PCT/US98/11007 on May 29, ~~2008~~ 1998, now Pat. No. 6,511,511.

Signed and Sealed this

Second Day of June, 2009

JOHN DOLL
*Acting Director of the United States Patent and Trademark Office*